(12) United States Patent
Koren et al.

(10) Patent No.: US 8,423,383 B2
(45) Date of Patent: Apr. 16, 2013

(54) CONTEMPORANEOUS, MULTI-PHYSICIAN, ONLINE CONSULTATION SYSTEM

(75) Inventors: Michael J. Koren, Ponte Vedra Beach, FL (US); Donald E. Dawson, Jacksonville, FL (US)

(73) Assignee: Jaxresearch Systems, LLC, Jacksonville, FL (US)

( * ) Notice: Subject to any disclaimer, the term of this patent is extended or adjusted under 35 U.S.C. 154(b) by 753 days.

(21) Appl. No.: 11/504,467

(22) Filed: Aug. 15, 2006

(65) Prior Publication Data

US 2008/0059237 A1   Mar. 6, 2008

(51) Int. Cl.
*G06F 19/00* (2006.01)

(52) U.S. Cl.
USPC .................................................. 705/3; 705/2

(58) Field of Classification Search ............... 705/2–4
See application file for complete search history.

(56) References Cited

U.S. PATENT DOCUMENTS

| | | | |
|---|---|---|---|
| 6,256,613 B1 * | 7/2001 | Falchuk et al. | 705/2 |
| 6,482,156 B2 | 11/2002 | Iliff | |
| 6,641,532 B2 | 11/2003 | Iliff | |
| 6,725,209 B1 | 4/2004 | Iliff | |
| 6,850,889 B1 | 2/2005 | Zayas, Jr. | |
| 7,051,012 B2 | 5/2006 | Cole et al. | |
| 7,306,560 B2 * | 12/2007 | Iliff | 600/300 |
| 2004/0078211 A1 * | 4/2004 | Schramm-Apple et al. | 705/1 |
| 2004/0181428 A1 * | 9/2004 | Fotsch et al. | 705/2 |
| 2006/0026502 A1 * | 2/2006 | Dutta | 715/511 |
| 2006/0184393 A1 * | 8/2006 | Ewin et al. | 705/2 |

OTHER PUBLICATIONS http://web.archive.org/web/20030207193711/www.relayhealth.com/.*

* cited by examiner

*Primary Examiner* — Robert Morgan
*Assistant Examiner* — Kristine Rapillo
(74) *Attorney, Agent, or Firm* — Epstein Drangel LLP; Robert L. Epstein

(57) ABSTRACT

The computer-implemented system of providing online medical consultation services by a team of medical professionals begins when a user accesses the system website. The user selects the level of consultation services desired and a case submission form is provided to the user requesting information relating to desired medical consultation. The user provides the requested information on case submission form. If additional information is required, it is obtained. When the case is ready for submission, members of the medical professional team are selected for consultation on the case and forwarded the particulars of the submitted case via the Internet. The selected team members review the submitted case particulars and each member provides their medical opinion via Internet. The submitted opinions are recorded and displayed in real time on the system website, to which the user has access. In addition, the submitted opinions to structured questions are compiled to determine if there is a consensus. A graphical representation of the compiled opinions is generated and displayed in real time on the website, as well. This system can provide nearly instant information as to the sum of the opinions of medical experts for a variety of case scenarios and establishes whether, and to what extent, a consensus exists among the consulting medical professionals.

88 Claims, 8 Drawing Sheets

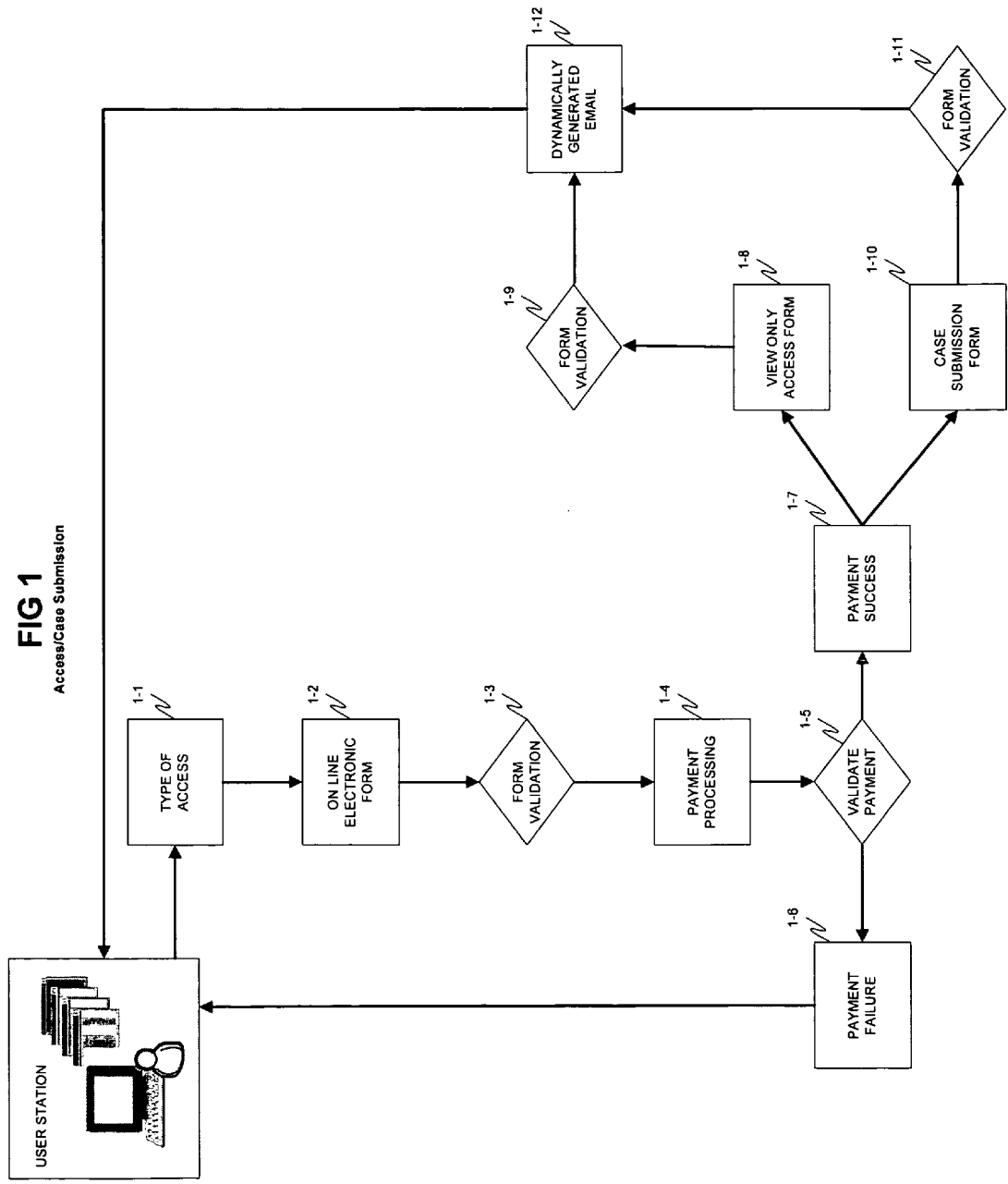

Email Process

Consumer Login part 1

Doctor/Medical Professional Approval

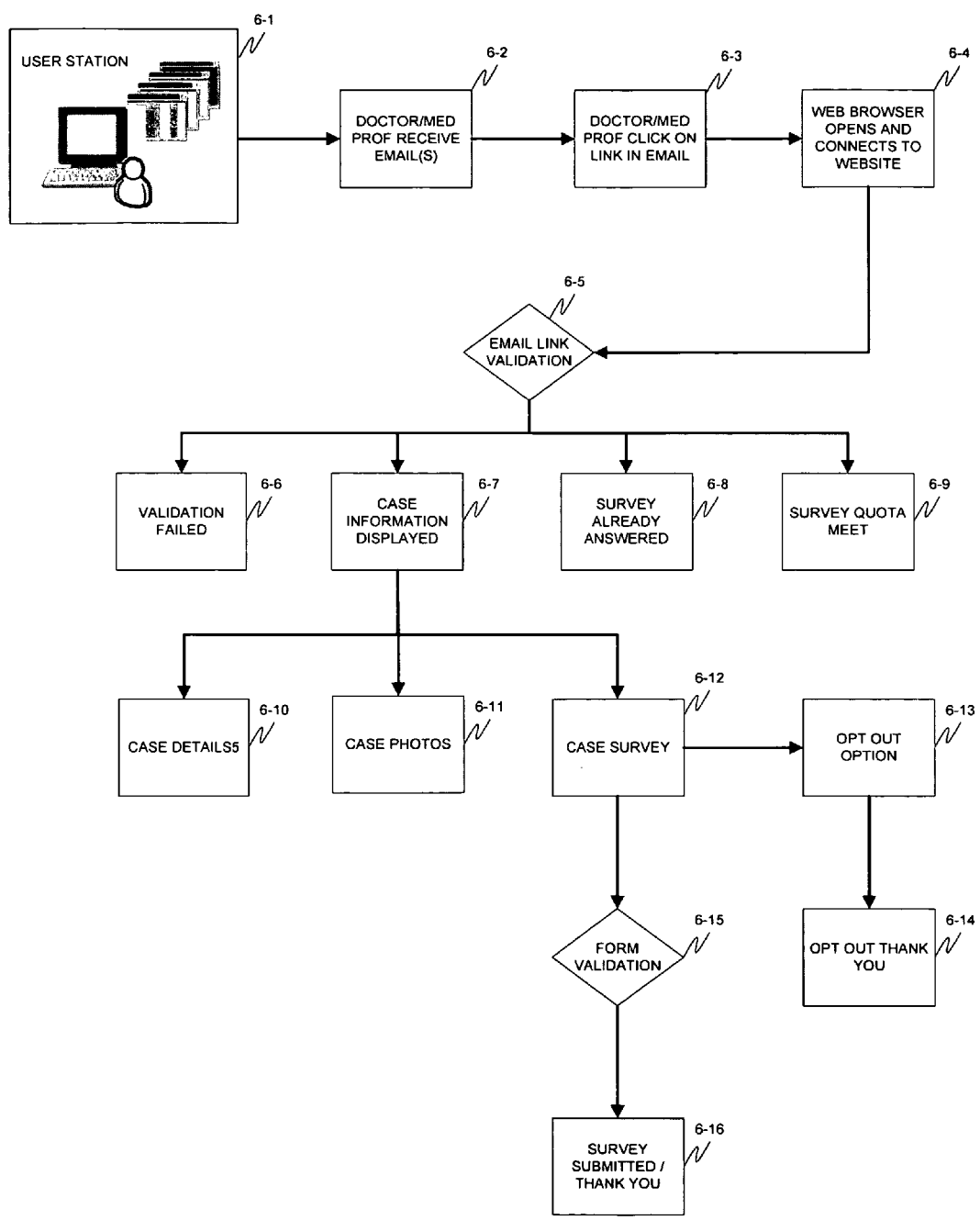

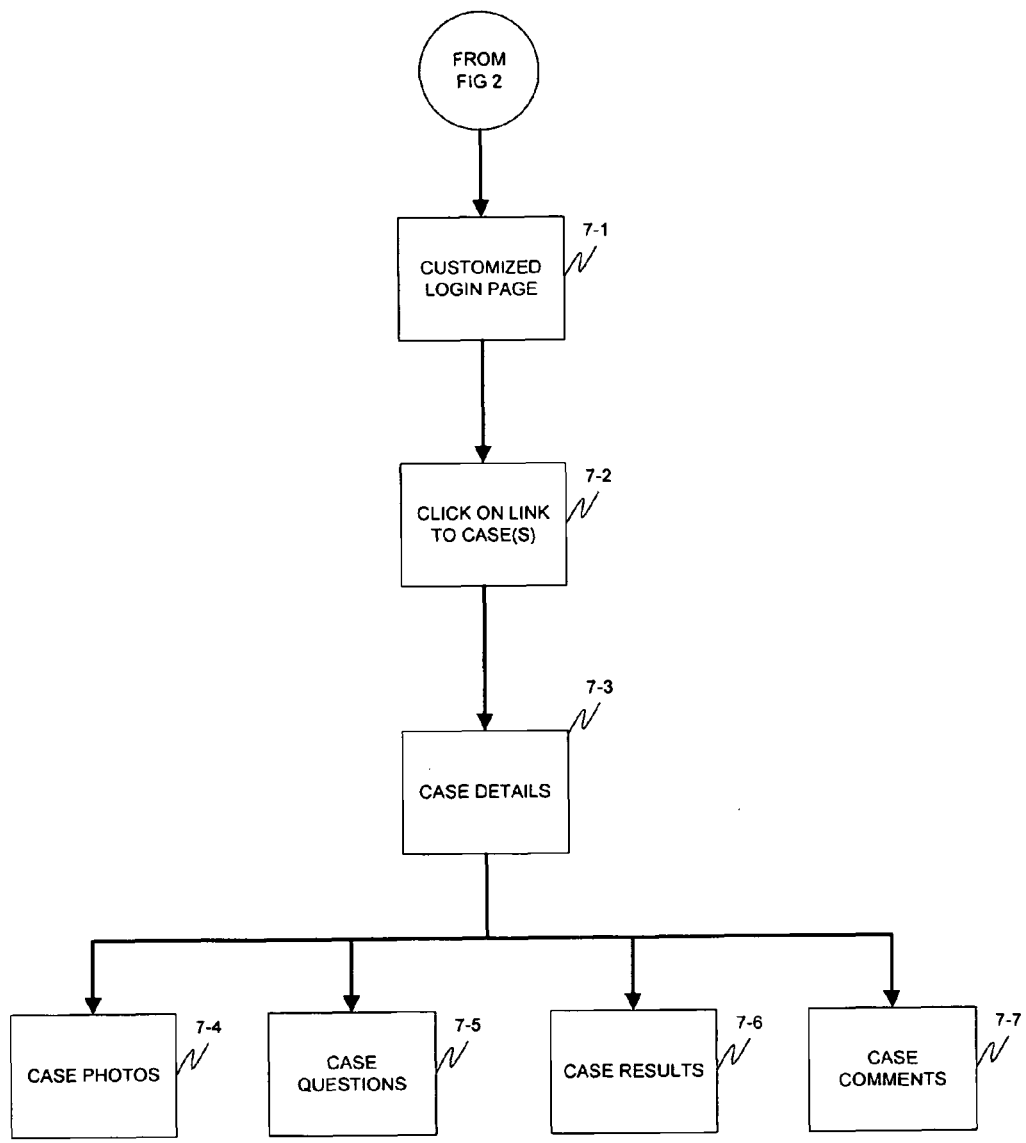

CONTEMPORANEOUS, MULTI-PHYSICIAN, ONLINE CONSULTATION SYSTEM

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to a medical consultation system and more particularly to a contemporaneous, multi-physician, online consultation system in which a user can obtain easily understandable medical opinions of many qualified, unbiased health care professionals and experts through the Internet. This system can provide information as to the sum of the opinions of medical professions for a variety of case scenarios and establish whether, and to what extent, a consensus of such opinions exists.

2. Description of Prior Art Including Information Disclosed Under 37 CFR 1.97 and 1.98

In the information age, effective decision making can be easily impaired by an overabundance of data. Internet access provides nearly limitless information on most subject matters. Ironically, these instantly available facts and opinions can paralyze rather than enhance decision making because capabilities to obtain information often overwhelm systems to meaningfully characterize and analyze the information received.

This dilemma is particularly true in health care fields where multiple sources of medical facts and opinions, often varying in strength and verifiability, inform medical decision making. This vast volume of medical data often presented in an unfamiliar format can lead to patient confusion. This confusion is further complicated by competing claims often arising from the dissemination of medical information by parties with proprietary interests in health care products or services.

The opinions of well intentioned qualified health care practitioners may also differ. Medical practitioners make recommendations based on their personal experiences and data known to them. Because of the vastness of medical information, health care practitioners may weigh medical information differently resulting in the rendering of patient medical opinions which may, in some cases, conflict with one another. If medical professionals can offer different medical advice for the same case scenario, it is not surprising that medically untrained patients can be easily confused and frustrated by the amount and variability of available medical information.

Ideally, patients should be able to review the best consensus opinions for all their health care concerns. Building a system to enable this consensus opinion generation would require access to qualified, unbiased, health care professionals who are familiar with and can apply their collective experience to an individual case. This system would also be able to rapidly evaluate data, be scaleable by numbers of health care providers or narrowness of expertise as cases require, and have an output that is produced contemporaneously, is easily understandable and reflects the weight of medical evidence when differences of opinion arise. In the perfect system, the health care providers would have adequate incentive to respond rapidly to patient scenarios once presented yet derive no personal gain that could bias recommendations when patients follow the opinions rendered.

Currently, efforts to create consensus opinions in medical fields occur through expert committees. These committees may be brought together by government entities or elements of organized medicine or medical industry. These committees are often charged with reviewing large bodies of medical information and crafting consensus statements when possible. Though the work of these groups is quite valuable, inevitably it is slow, often non-specific and cannot address the nuances of medical care relevant to individual patients.

Because of these limitations, an individual patient who seeks to obtain a consensus medical opinion on his or her specific health care circumstances can not be sure if this goal is met. At best, he or she could seek the advice of a physician and perhaps a second opinion or two and trust that this advice is in line with consensus. He or she may also do personal research using a vast variety of medical sources. Unfortunately, except for the exceptionally educated patient perhaps, finding a consensus of opinion would be more guesswork than science.

The present invention relates to a system that provides for contemporaneous multi-physician consultations and an output to allow patients to easily understand the strength of consensus medical views. It uses information technology systems integrated with human resources to produce an output that quickly enables case by case generation of consensus opinions for health care matters or establishes that no consensus exists. The system also compensates health care providers for their expertise without creating financial incentives that can bias decision making. Based on our review of the medical literature and prior art, no system for providing contemporaneous, simultaneous multiple physician consultations with a user friendly output exists.

It is, therefore, a prime object of the present invention to provide a system providing contemporaneous, simultaneous multiple physician consultations with a user friendly output.

It is a further object of the present invention to provide a system for providing contemporaneous, simultaneous multiple physician consultations through the Internet.

It is a further object of the present invention to provide a system for providing contemporaneous, simultaneous multiple physician consultations wherein the individual opinions of the consulting physicians are reported to the user in real time.

It is a further object of the present invention to provide a system for providing contemporaneous, simultaneous multiple physician consultations wherein the sum of the opinions of the consulting physicians is reported to the user in real time.

It is a further object of the present invention to provide a system for providing contemporaneous, simultaneous multiple physician consultations wherein whether, and to what extent, a consensus of the opinions of the consulting physicians is present is reported to the user through a graphical representation.

BRIEF SUMMARY OF THE INVENTION

The above objects are achieved by the present invention which relates to a computer-implemented system of providing online medical consultation services by a team of medical professionals. The system is accessed by a user who connects to a website. The user selects the level of consultation services desired. The user is provided with a payment demand, based upon the level of services selected. The user submits the payment information on a form provided. The submitted payment information is verified.

A case submission form is then provided to the user requesting information relating to desired medical consultation. The user provides the requested information on case submission form.

The submitted information on the case submission form is reviewed by a medical professional. A determination is made if additional information is required to process a case. If so, the additional information is requested from the suitable source. It is determined if the case is ready for processing at that point.

When the case is ready for submission to a panel of medical professionals, members of the professional team are selected for consultation on the case. The system employs a software program to select appropriate medical professionals from a database. Selections from the database can be sorted by various characteristics of the medical professionals such as age, medical specialty, gender or geographical location. The selected professionals are forwarded the particulars of the submitted case via the Internet and e-mail. Structured questions are submitted with the particulars of each case. The selected medical professionals review the submitted case particulars and each member provides their medical opinion via Internet.

The submitted opinions are recorded and answers to structured questions are tallied. The opinions are also displayed in real time on the system website to which the user has access.

In addition, the submitted opinions are compiled to form a graphical representation of the compiled opinions. The graphical representation is displayed on the website to illustrate if, and to what extent, a consensus of opinion exists among the polled professionals.

The step of reviewing information on the provided case submission form includes parsing the information on the case submission form and comparing same to defined criteria using a software program. The user is notified if information is not acceptable. In that case, the user is permitted to revise the unacceptable information. The revised information is parsed and stored, if acceptable.

The system also includes a program that generates a message to the user via the Internet including instructions for logging into a website using a user name and password.

Further, assets consisting of text, graphics, animations, audio and video information relating to the case are stored. One or more of the stored assets are selected. The selected assets may be utilized to create the message to the user.

The step of verifying payment information includes notifying the user if the payment is not validated.

The system further allows a "view only" option that provides a user with access to cases stored in the website displaying the medical opinions. A user can find various types of cases previously reviewed by medical professionals using a system specific search engine, if the "view only" option is selected.

The level of services selected by user determines the extent the user can access the website with displayed opinions. It also determines the complexity of the case that a user may submit for consultation.

The system also includes computer-implemented software to select and register medical professions for participation. That is done by inviting potential medical professionals to participate and providing each potential medical professional that agrees to participate with website login information. When the professional successfully logs into the website, a welcome message is sent. The professional is provided with a contract for signature, which is signed and returned. The information on the signed contract is validated. Personal and/or professional information is solicited from each medical professional with a validated contract. The information provided by the medical professional is further validated and stored. Approval of the medical professional as a member of team is then confirmed.

The system includes software that periodically checks the website for new case submissions. The step of determining if additional information is required to process the case and, if so, requesting same, includes forwarding information to a health care provider who reviews each new case submitted. If the selected level of the submitted case requires user interaction, the user is contacted. The case is reviewed with contacted user and additional information is obtained from contacted user, if necessary.

The system further allows for one or more structured questions to be generated relating to a submitted case. The system also compiles one or more answers to the questions and stores the questions and answers.

The step of selecting members of the team for consultation on the case includes sending a survey to each selected member of the team; reviewing the survey results; and posting the survey results in real time.

The step of selecting members of the team for consultation on the case also includes reviewing previously stored information about members of the team; and selecting members for consultation on the submitted case based upon the reviewed information.

The step of selecting members of the team for consultation includes retrieving a list of approved medical professionals; selecting a medical professional from the list; reviewing previously stored information about the medical professional selected from the list and comparing same with defined criteria.

The step of advising selected team members of the particulars of the case via the Internet includes contacting a selected team member to notify him or her that there is a case for consultation; providing the contacted member with a link to the website; displaying the case particulars on the website; and providing a survey to the member for recording his or her opinion.

The system also determines if the survey was already answered by the contacted member and determines if the survey quota has already been met.

The system also allows a selected health care professional to opt out of participation in the consultation and makes note of this decision.

The step of displaying the case particulars includes displaying detailed information about the case on the website. It also includes displaying images relating to the case on the website.

The system also includes a provision for the user to log onto a website, select a case, view the details of case, view case questions, view the displayed opinions from team members and view displayed case comments from the team members.

The step of having the selected health care professionals review the case and submit an opinion includes providing the team member with a survey to report his or her opinion regarding submitted case and displaying the survey results on a website. The survey results are displayed on the website in real time.

The step of generating a graphical representation of the survey results includes displaying same on the website in real time.

BRIEF DESCRIPTION OF THE SEVERAL VIEWS OF DRAWINGS

To these and to such other objects that may hereinafter appears, the present invention relates to a contemporaneous, multi-physician, online consultation system as described in detail in the following specification and recited in the annexed claims, taken together with the accompanying drawings, in which:

FIG. 1 is a system flowchart overview and describes the components and functionality of the consumer access/case submission system;

FIG. 1A describes the components and functionality of the Dynamically Generated Email system;

FIG. 6 is a detailed flowchart and shows the process in which a doctor/medical professional sees (on any Web accessible device) and goes through to submit answers to the surveys emailed to them; and FIG. 7 is a detailed flowchart and is a continuation of the login process from FIG. 2.

DETAILED DESCRIPTION OF THE INVENTION

Figure 1A:
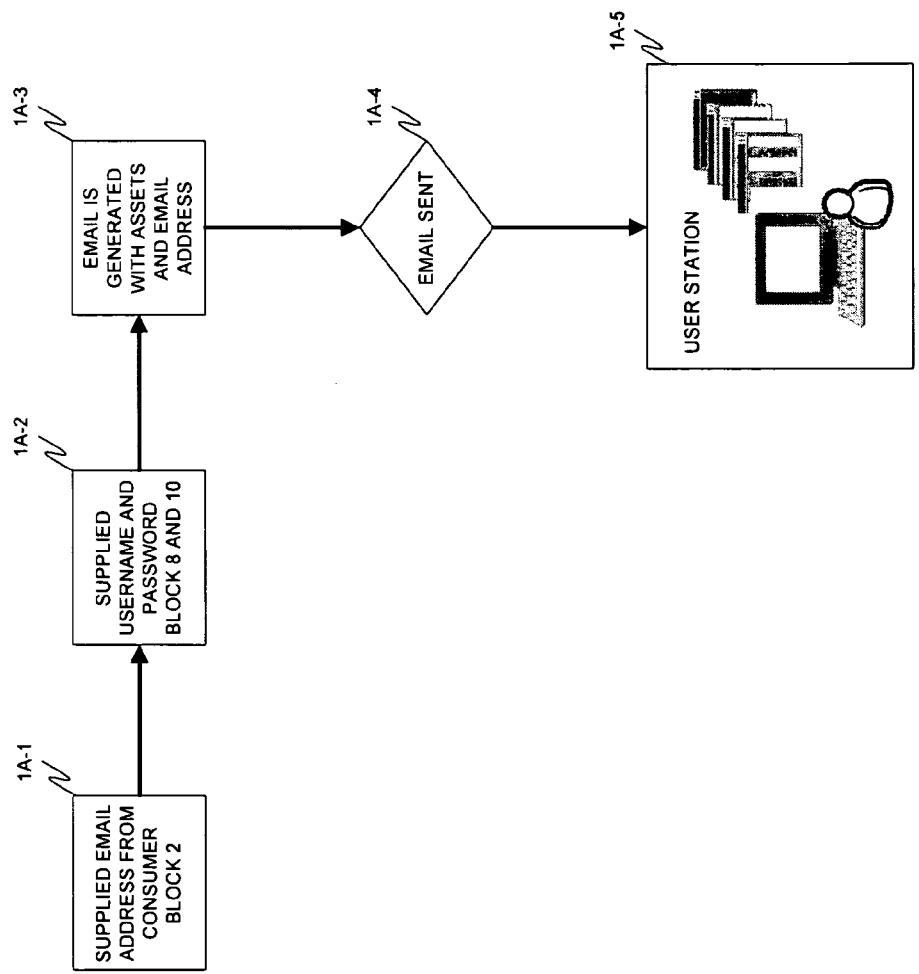

The different figures presented illustrate the steps involved in implementing the system of the present invention. However, it should be understood that the figures show only one preferred embodiment of the invention for purposes of illustration and that numerous modifications could be made thereto without deviating from the general concept of the present invention.

FIG. 1 is a system flowchart overview and describes the components and functionality of the consumer access/case submission system. The block numbers in FIG. 1 match the Block numbers below.

Block 1-1—Type of Access. The user of the system indicates which type of access and/or medical case to submit. The different types of access/submissions include, for example, a temporary pass which can be defined in hours, days, etc, a full pass which allows access for set period of time (ie. a number of months or years), and submission of a medical case at different levels of complexity. The selected type of access will determine what type of form and amount of payment is required and sent to the display screen of the computer of the user. Once the type of access is selected, the user is sent to the Online Electronic Form.

Block 1-2—OnLine Electronic Form. The user fills out the online form from a User Station (ie: PC, WebTV, Handheld or any other web capable device). This form will gather input from the user that will be validated at submission.

Once the form is completed, the user submits the form electronically to the systems server by clicking on a submit button that is on the display screen of the user. Transmission can be done through either wire or wireless communications.

Block 1-3—Form Validation. The submitted form data are then parsed through via software code against defined criteria. The form data must meet minimum defined criteria to be accepted for processing. If a section of the form data is not acceptable, the user is notified with a screen on their display. The user is allowed to correct the unacceptable data. Once corrected, or if all data are considered acceptable, the form data are submitted for data processing.

Block 1-4—Payment Processing. The form data that were submitted are added to a database. A list of payment options, such as PayPal, Visa, Mastercard, etc (any type of payment whether electronic or mailed in) will be sent to the user display. Once the user has selected the type of payment, and submits the required amount of payment, the user is redirected to a results display that validates the payment.

Block 1-5—Validate Payment. If payment was unsuccessful for any reason, the user is directed to a failure of confirmation page which is sent to their display.

Block 1-6—Payment Failure. If the processing of payment was rejected, declined or unsuccessful for any reason in Block 1-5, the user is displayed with a payment failed screen and, if available, the reason of the failure will be displayed. The user may resubmit for processing by starting at Block 1-1.

Block 1-7—Payment Success. Upon successful payment, the user will be redirected to an electronic form which will request certain information depending on which type of access/case the user has selected. The types of forms are explained in Block 1-8 and Block 1-10 below.

Block 1-8—View Only Access Form. This is an electronic form that allows the consumer to create a Username and Password that they will use to access the Secure Login Area.

Block 1-9—Form Validation. The submitted form data are parsed through via software code against defined criteria. The form data must meet minimum defined criteria to be accepted for processing. If a section of the form data is not acceptable, the user is notified with a screen on their display and allowed to correct the unacceptable data. Once corrected, or if all data are considered acceptable, the form data are submitted for data processing.

Block 1-10—Case Submission Form. This form is used to gather input from the file up to the system server. The form also allows the user to create a Username and Password that they will use to access the Secure Login Area.

Block 1-11—Form Validation. The submitted form data are then parsed through via software code against defined criteria. The form data must meet minimum defined criteria to be accepted for processing. If a section of the form data is not acceptable, the user is notified with a screen on their display and allowed to correct the unacceptable data. Once corrected, or if all data are considered acceptable, the form data are submitted for data processing.

Block 1-12—Dynamically Generated Email. The submitted form data from Block 1-9 and Block 1-11 are then added to the database. From the data gathered in the database, an email is dynamically generated and delivered in real-time by electronic means to the user's supplied email address through wire or wireless communications. The email contains a welcome message, instructions for logging into the system along with the Username and Password that the user created in Block 1-8 and Block 1-10.

All of the assets of the dynamically generated emails are stored on the secured server (computer where the website exists) that are used in the system described in FIG. 1A. These assets can consist of text, graphics, animations, audio and video information. These dynamically generated emails can comprise some combination of these assets. All assets used for the dynamically generated emails can be changed based upon submitted user data, as well as company needs. There is no limit to the number and type of dynamically generated emails that can be created and delivered.

FIG. 1A illustrates the components and functionality of the Dynamically Generated Email system.

Block 1A-1. Email addresses that were gathered and stored in the database from FIG. 1 Block 1-2 are retrieved.

Block 1A-2. Username and Passwords that were gathered and stored in the database from FIG. 1 Blocks 1-8 and 1-10 are retrieved.

Block 1A-3. All information from Blocks 1-1 and 1-2 are assembled into an email message to be sent to the consumer.

Block 1A-4. The dynamically generated email is emailed to the consumer's email address. Information in the message may include but is not limited to: a welcome message, login information, privacy information, combination of assets, etc.

Block 1A-5. The user receives the email.

Figure 2:
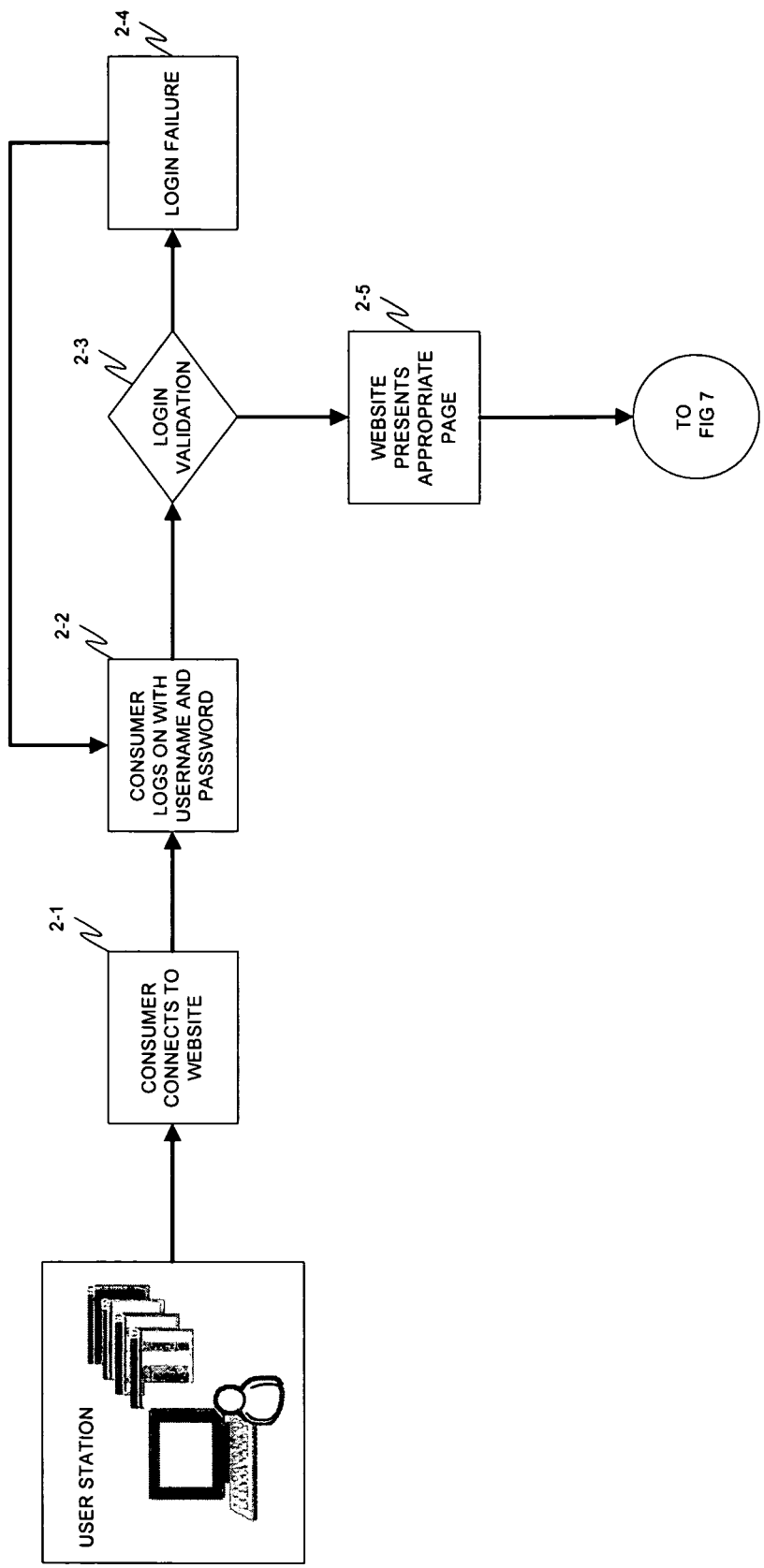
FIG. 2 is a detailed flowchart and shows the steps from when the consumer connects to the website until they are presented with the appropriate data and access.

FIG. 2 is a detailed flowchart and shows the steps from when the user connects to the website until they are presented with the appropriate data and access.

Block 2-1. User connects to the website from a web accessible device and navigates to the page that allows the user to enter in their username and password.

Block 2-2. User utilizes the username and password that they created when they filled out the electronic form from FIG. 1 Block 1-2 and was emailed to the consumer.

Block 2-3. The provided username and password is then used to search the database of existing data to verify that the username and password presented is correct. If there is no match in the database to the username and password provided then the user is redirected to a Login Failure page, Block 2-4, or if a successful match was found, the user is redirected to a page that is dynamically generated based on level of access, Block 2-5.

Block 2-4. If the user provided username and password is incorrect, they will be redirected to this failure page informing them that either the username or password was incorrect. It also allows them to click on a link/button that redirects them back to the logon page, Block 2-2, so that they can repeat the login process.

Block 2-5. If the user provided username and password is correct, they will be redirected to a web page that is dynamically generated showing or hiding sections of the website based on the level of access the user chose during the access/case submission process, FIG. 1 Block 1-1

Figure 3:
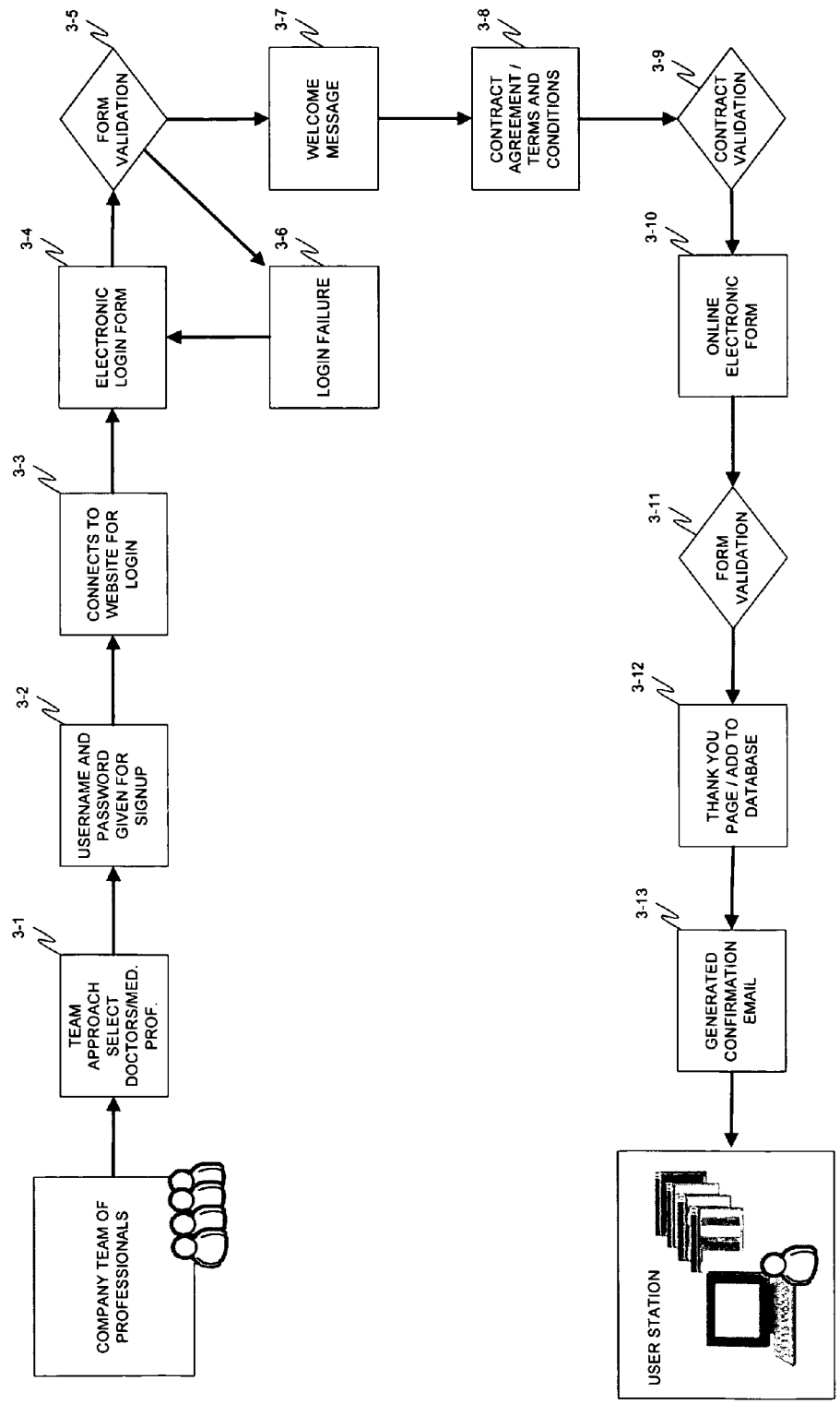
FIG. 3 is a detailed flowchart and shows what the doctors/medical professionals see (on any Web accessible device) as they go through the Signup process.

FIG. 3 is a detailed flowchart and shows what the doctors/medical professionals see (on any Web accessible device) as they go through the Signup process. It is important to note that this is not the only method for signing up doctors/medical professionals and adding them to our database for future use and processing. They can be signed up and added by phone, email, fax or any other means of communication or added to the database via webpage, programming code, or other means of database communications.

Block 3-1. The team of professionals approaches doctors/medical professionals inviting them to participate in part of our system of answering surveys.

Block 3-2. If the doctors/medical professionals from Block 3-1 agreed to participate, they receive a username and password along with a website address for the signup process to continue. The username, password, and website address can be given over the phone, email, pager or any other means of communications.

Block 3-3. Once the doctors/medical professionals obtain the username and password, they connect via any web capable device connecting to the provided web site address.

Block 3-4. The doctors/medical professionals input the username and password and click a submit button on an electronic form.

Block 3-5. The submitted username and password is then used to search the database of existing data to verify that the username and password presented is correct. If there is no match in the database to the username and password submitted, the doctor/medical professional is redirected to a Login Failure page, Block 3-6, or if a successful match was found, the doctor/medical professional is redirected to a welcome page, Block 3-7.

Block 3-6. If the submitted username and password was incorrect, a Login Failure page will be displayed notifying them that the username and password was incorrect. They will also be presented with a link back to the electronic login page, Block 3-4.

Block 3-7. If the submitted username and password was correct, a Welcome page will be displayed notifying them the login was successful. This may contain assets including but not limited to text, animations, audio, video, etc. Once the doctors/medical professionals have finished with the welcome page they will have a link allowing them to continue with the signup process taking them to the Contract Agreement/Terms and Conditions page, Block 3-8.

Block 3-8. In order for each doctor or medical professional to participate in the survey system they must have read and signed a contract agreement agreeing to the terms and conditions of the system. This can be accepted in either paper or electronic form. In order to continue, they must select the electronic form that they have read and agree to the contract. The provided link will allow them to submit the agreement for validation.

Block 3-9. The submitted form data are then parsed through via software code against defined criteria. The form data must meet minimum defined criteria to be accepted for processing. If a section of the form data is not acceptable, the doctor/medical professional is notified with a screen on their display and allowed to correct the unacceptable data. Once corrected, or if all data are considered acceptable, the form data are submitted for data processing.

Block 3-10. This form will gather input from the doctors/medical professionals that will be validated at submission. The information gathered may include but not limited to personal, geographical and professional information.

Block 3-11. The submitted form data are then parsed through via software code against defined criteria. The form data must meet minimum defined criteria to be accepted for processing. If a section of the form data is not acceptable, the doctor/medical professional is notified with a screen on their display and allowed to correct the unacceptable data. Once corrected, or if all data are considered acceptable, the form data are submitted for data processing.

Block 3-12. After successful submission of form data the doctors/medical professionals are then redirected to a successful page. The data submitted are also added to the database.

Block 3-13. Once the data have been added to the database, an email is generated and sent to doctor/medical professional with confirmation completing the signup process.

Figure 4:
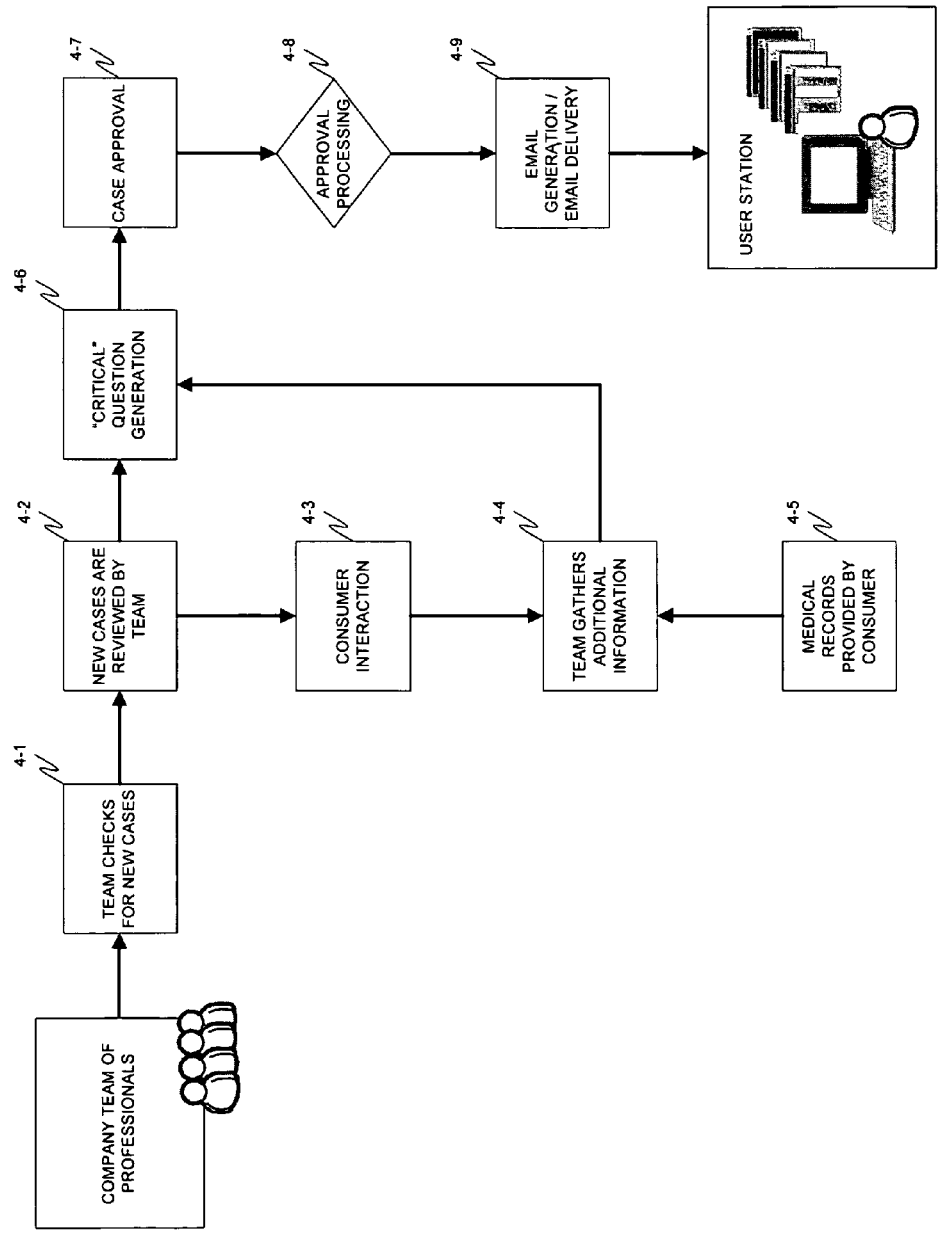
FIG. 4 is a detailed flowchart and shows what the Case Approval process is after the consumers have submitted a case.

FIG. 4 is a detailed flowchart and shows what the Case Approval process is after the users have submitted a case.

Block 4-1. A team of company professionals connect to the website and check for newly submitted case.

Block 4-2. The team then reviews all newly submitted cases. They take each case and make sure that it is properly formatted; text and submitted photos are cleaned for public viewing, etc. Depending on the level of case submitted, it may require interaction with the consumer who submitted the case, Block 4-3, or the case may be reviewed and sent on to the next step without consumer interaction, Block 4-6.

Block 4-3. If the level of submitted case requires consumer interaction, someone from the team will contact the user via email, phone, cell, or any other means of communication.

Block 4-4. The team member will review the submitted case with user and gather additional information about the submitted case to better construct a presentable case.

Block 4-5. If necessary, the team will request medical records that will assist them in creating the survey questions. These records can be transmitted by fax, mail, electronic or any other means of transmission.

Block 4-6. Once the cases have been reviewed and all necessary information and documents have been gathered, the team will then begin the "Critical" Question Generation process. During this process, the team will generate a survey question or multiple survey questions. The number of questions will vary from case to case. Along with each question, the team will generate answers and the number of answers will vary question to question. All questions and answers are added to the database.

Block 4-7. When all the questions and answers have been generated, the case details have been reviewed and the photos have been reviewed, the case has one final review and then is ready for the selection process.

Part of the approval process is the selection of doctors/medical professionals to receive the case. The selection of doctors/medical professionals and selection criteria may vary from case to case. The approval selection can send the survey to all doctors/medical professionals or to a selected list based on criteria such as but no limited to geographical location, profession specialties, age, gender, and various other collected information that is stored in the database. After the selection process the case is approved.

Block 4-8. The selection of criteria is processed and added to the database and prepares the data from the approval page and retrieved database data for email processing.

Block 4-9. An email is generated for each of the selected doctors/medical professionals and delivered by email. The email contains information identifying the email with the survey system, a website link back to the actual survey, policy information, and other asset related material such as, but not limited to text, images, animations, audio and video.

Figure 5:
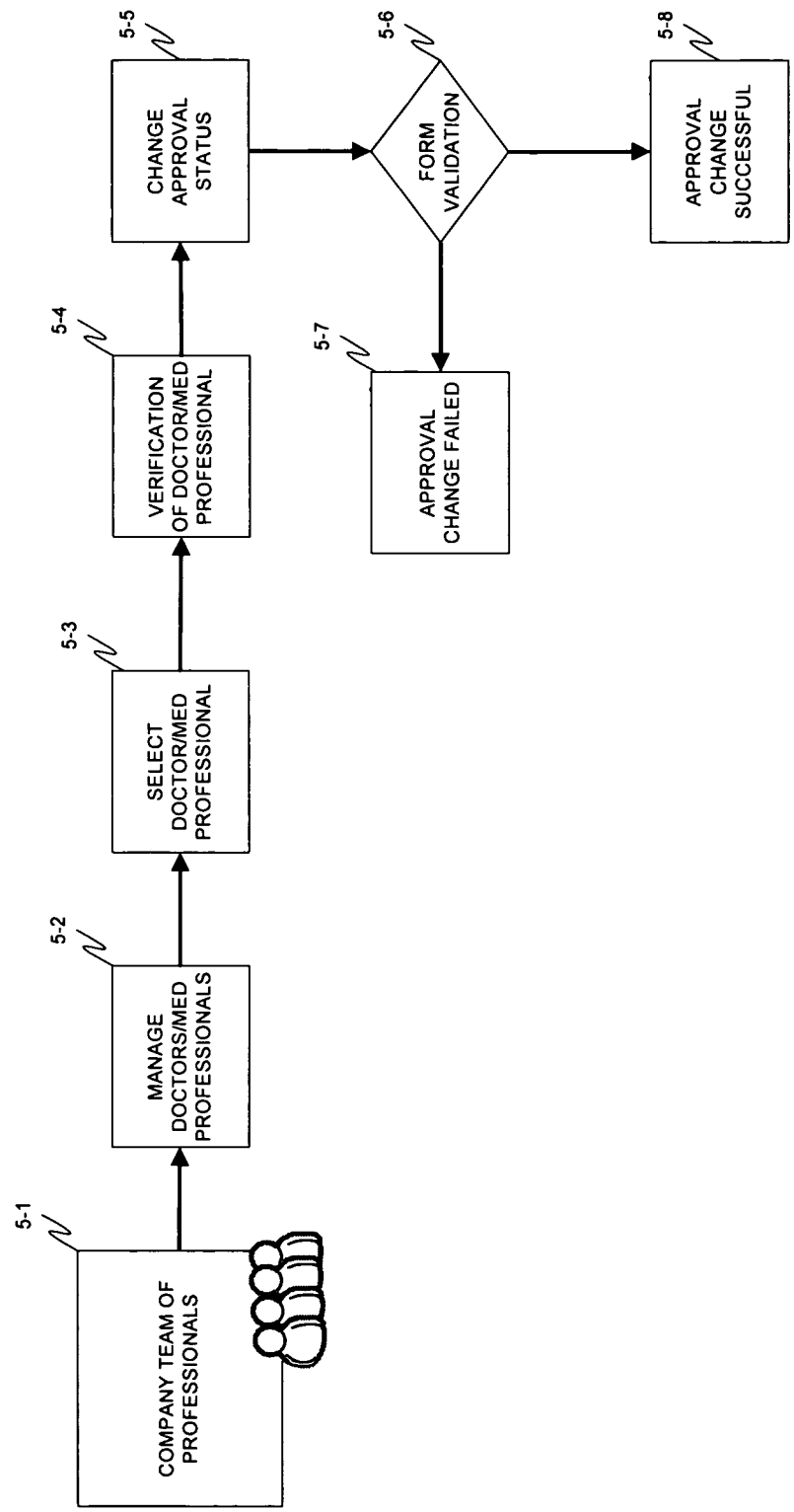
FIG. 5 is a detailed flowchart and shows what the Doctor/Medial professional approval process is after doctors/medical professionals have completed the Signup process.

FIG. 5 is a detailed flowchart and shows what the Doctor/Medial professional approval process is after doctors/medical professionals have completed the Signup process.

Block 5-1. The team members connect to a website that manages the data in the database. The data in the database can also be managed using other methods that can connect to and make changes to the database.

Block 5-2. The team members then click on Manage Doctors/Medical Professionals.

Block 5-3. This will retrieve and display a list of doctors/medical professional from the database. The team members locate and select the doctor/medical professional in question.

Block 5-4. The doctor/medical professional data are displayed and can include but are not limited to personal data, professional data, approval status, etc. In order for our select panel of doctors/medical professionals to receive the emails that allow them access to the cases/surveys they have to have an approval status.

Block 5-5. The team members then review and cross-check information about the doctor/medical professional to verify credentials. Once the verification is complete, the status of the doctors/medical professionals is changed to Approved. After the status or any other changes have been made, the team member submits the data for validation.

Block 5-6. The data in the submitted form are parsed through via software code against defined criteria. The form data must meet minimum defined criteria to be accepted for processing. If a section of the form data is not acceptable, the team member is notified with a screen on their display and allowed to correct the unacceptable data. Once corrected or if all data are considered acceptable, the form data are submitted for data processing.

Block 5-7. If the submitted changes failed to update the database, a failure status page is displayed.

Block 5-8. If the submitted changes were successfully updated in the database, a successful page is displayed.

FIG. 6 is a detailed flowchart and shows the process which a doctor/medical professional sees (on any Web accessible device) and goes through to submit answers to the surveys emailed to them.

Block 6-1. The selected doctors/medical professionals check and receive the system email(s).

Block 6-2. The doctors/medical professionals review the email received from the system (on any web accessible device)

Block 6-3. They click on the link provided in the email or they may be able to type in the website address if needed in any web capable browser.

Block 6-4. The clicked email, Block 6-3, will open up a web capable browser that is loaded on their computer system and connects to the destination website.

Block 6-5. Once the web browser connects, the web site page and programming code does an email link validation to ensure the person connecting to the site is allowed to proceed. If the email link was not properly formatted or if the website address was typed in incorrectly, the doctors/medical professional is redirected to a validation failure on their display, Block 6-6.

If the link or typed in information was properly formatted, the validation process checks the database to see if the doctor/medical professional has already answered and if so they are redirected to a display notifying them that they have already answered this case/survey, Block 6-8, otherwise if they have not answered the case/survey then they are presented with the case details/survey on their display, Block 6-7.

The validation process also checks to see if the maximum number of answers has been met for that particular case/survey. If the survey quota have been meet, the doctors/medical professionals are then redirected to a display notifying them that the case/survey quota have been met, Block 6-9, otherwise if the survey quota for this particular case/survey have not been met, they are presented with the case details/survey on their display, Block 6-7.

Block 6-6. If the link was incorrectly formatted or manually typed incorrectly in the web browser, a validation failed will be displayed along with contact and next step information.

Block 6-7. After all validation, Block 6-5, has been completed and all conditions have passed successfully, the actual case details/survey is presented to their display.

Block 6-8. If the validation, Block 6-5, has determined that the doctor/medical professional has already answered the particular survey, a page will be displayed notifying them that they had already answered this survey and any other information that we may want to present.

Block 6-9. If the validation, Block 6-5, has determined that the case/survey quota have been met and is not accepting any more survey answers, a page will be displayed notifying them that the survey quota have been met and any other information that we may want to present.

Block 6-10. From Block 6-7, the doctors/medical professionals are now presented with the actual case details that have been retrieved from the database.

Block 6-11. This section shows any photos or images associated with the case details and display them on the doctors/medical professional's screen.

Block 6-12. This section shows the survey questions/answers that were generated, FIG. 4 Block 4-6, in the Case Approval process along with other form elements like a comments field.

The doctors/medical professionals are presented with two options. One is to "Opt Out" of the survey, Block 6-13. The other option is to answer the survey and submit their answers for validation, Block 6-15.

Block 6-13. If the doctor/medical profession has chosen to "Opt Out" of the survey, it is recorded into the database and does not count toward the survey quota. This also restricts the doctor/medical professional from coming back and answering, Block 6-8.

Block 6-14. After the doctor/medical professional "Opt Out" status has been recorded into the database, they are redirected and displayed a "Thank You" page.

Block 6-15. If the doctor/medical professional decided to answer the survey, the submitted answers from Block 6-12 are parsed through via software code against defined criteria. The form data must meet minimum defined criteria to be accepted for processing. If a section of the form data is not acceptable, the doctor/medical professional is notified with a screen on their display and allowed to correct the unacceptable data. Once corrected or if all data are considered acceptable, the form data is submitted for data processing.

Block 6-16. Once the submitted survey data has been validated it is then recorded into our database and the doctors/medical professionals are redirected to a display notifying them that their data have been submitted and a "Thank You".

FIG. 7 is a detailed flowchart and is a continuation of the login process from FIG. 2.

Block 7-1. After the customer submits their username and password, FIG. 2 Block 2-2 and the validations are successful, the customer is presented a dynamically generated page that is customized to their type of access.

Block 7-2. If a customer has submitted a case, their cases will be displayed. The customer then clicks on the particular case link they want to view to review case details.

Block 7-3. The case details are displayed with links to other areas of the case, such as but not limited to, case photos, questions, results, etc.

Block 7-4. If a photo was submitted during the sign up process, FIG. 1 Block 1-10, then the clicking on the Images link will display any associated photos.

Block 7-5. The questions that were generated in FIG. 4 Block 4-6 will be displayed when they click on the Questions link.

Block 7-6. The Results page shows the answers in real time as the doctors/medical professionals answer the surveys. The questions and answers are listed along with a graphical representation of the results illustrating the consensus of the opinions recorded on the surveys. The layout or presentation of results is designed to be user friendly such that the user can readily ascertain the individual opinions of the consulting professionals as well as the consensus of the opinions.

Block 7-7. As doctors/medical professionals complete surveys, FIG. 6 Block 5-12, they can submit comments about the case. These comments are displayed in real time when the customer clicks on the Comments link.

It will now be appreciated that the present invention relates to a computer implemented system of providing online medical consultation services by a team of medical professionals. The method begins when a user accesses the system website. The user selects the level of consultation services desired. The user is provided with a payment demand, based upon the level of services selected. The user submits the payment information on a form provided. The submitted payment information is verified. A case submission form is then provided to the user requesting information relating to desired medical consultation. The user provides the requested information on case submission form.

The submitted information on the case submission form is reviewed. A determination is made if additional information is required to process case. If so, the additional information is requested from the suitable source. When the case is ready for submission, members of the medical professional team are selected for consultation on the case. The selected members are forwarded the particulars of the submitted case via the Internet and e-mail. The selected team members review the submitted case particulars and each member provides their medical opinion via Internet.

The submitted opinions to "Critical Questions" for each case are recorded and displayed in real time on the system website to which the user has access. In addition, any submitted comments are compiled. A graphical representation of answers to structured questions and compiled opinions is generated and displayed in real time on the website. Users can quickly view the graphical display and understand whether or not a case has generated a consensus opinion among the responding medical professionals and understand the strength of the consensus, when same exists.

The system of the present invention has a variety of possible applications beyond simply providing the opinions of medical professionals to a patient in order to assist the patient in making a decision as to medical care. For example, the results of the medical opinions, and the strength of the consensus thereof, could be used by potential litigants or their attorneys in deciding whether or not to proceed with a medical malpractice lawsuit based on deviations from a standard of care consensus, to determine what the strength of a lawsuit based on consensus opinions would likely be and whether (or the amount of) a settlement should be considered. It could also be used in arbitration of medical disputes where an award could be based upon the opinions of a number of doctors (an unbiased source) indicating whether a particular course of therapy was within the accepted norm.

The system could be used in public relations or media, for example, where a quick and accurate poll of physicians is needed. This is an area where the number of physicians consulted could be increased to include any number of the database physicians to provide an instant or real time survey or consensus assessment of newsworthy medical items/stories, or an instant or real time assessment of government health policies, for example.

The system also has commercial applications. It could be use to provide an instant or real time consensus relating to a new drug or device, instant or real time health care provider focus groups on medical issues, or instant or real time competitive health assessments, for example, information as to whether the availability of a particular new drug would completely replace need for a pre-existing drug or whether a generic form of a particular drug would make proprietary versions of that drug unnecessary.

The system could be used in formulating health policy. It could be used to measure the acceptance level of a particular policy where the survey questions are designed to elicit physician opinion on upcoming policy, or measure the acceptance level of a certain public health official to determine whether such an individual might be elected to a position, such as the amount of political support for proposed or current FDA Commissioner, for example.

It has applicability in personal physician practices to demonstrate that physicians give advice differently when advising a family member as compared to recommendations for a typical patient. For newer technologies that appear promising but are unproven, the system of the present invention could be used to determine whether a consensus of physicians would use the new technology to treat their own families as a good way for the public to understand when doctors are practicing defensive medicine as opposed to following their true beliefs. Further, the surveys provided by the system could be used to elicit instant/real time physician health behaviors, for example, How much do they exercise? Do they take certain vitamins? etc.

The system of the present invention could be used with health care providers other than doctors. The team of medical professions could consist of or include nurses, chiropractors, pharmacists, etc., as well as or instead of physicians.

While only a single preferred embodiment of the present invention has been disclosed for purposes of illustration, it is obvious that many modifications and variations could be made thereto. It is intended to cover all of those modifications and variations which fall within the scope of the present invention, as defined by the following claims.

We claim:

1. A method of providing a consultation of medical professionals utilizing a computer-implemented system connected to the internet, integrated with human resources provided by professionals affiliated with the system, to form a consensus of opinions by a panel of medical professionals selected by the system but not provided with financial incentives which could bias their decision making, the method comprising the steps of:
   (a) creating a database of potential participating medical professionals, along with information about each the potential participating medical professionals, including the qualifications of the potential participating medical professionals;
   (b) user seeking a medical consultation accesses the system;
   (c) user submits information to the system regarding the desired medical consultation;
   (d) at least one professional affiliated with the system reviews information submitted by the user and structures one or more questions, based upon the user submitted information, for consideration by a panel of potential participating medical professionals selected from the database;
   (e) medical professionals qualified to provide response(s) to the structured question(s) are selected by the system to form a panel to provide responses to the structured question(s) based upon information in the database;
   (f) the structured question(s) are provided electronically to the medical professionals in the selected panel;
   (g) the medical professionals in the selected panel review the structured question(s) and provide responses thereto;
   (h) responses from the medical professionals in the selected panel are forwarded electronically to the system; and
   (i) system compiles responses, calculates the degree of consensus of the responses, and displays the calculated degree of consensus on a system website accessible to the user.

2. The method of claim 1 further comprising the step of at least one professional affiliated with the system administrator gathers additional information in order to structure question(s).

3. The method of claim 1 further comprising the step of at least one professional affiliated with the system administrator interacts with user to gather additional information about the desired consultation of medical professionals.

4. The method of claim 1 wherein user seeking a consultation of medical professionals accesses the system via the internet.

5. The method of claim 1 wherein user seeking a consultation of medical professionals submits information regarding the desired consultation of medical professionals to the system via the internet.

6. The method of claim 5 wherein a case submission form is provided to user seeking a consultation of medical professionals and user submits information regarding the desired consultation of medical professionals to the system using the case submission form.

7. The method of claim 6 wherein user submits information regarding the desired consultation of medical professionals to the system over the internet using the case submission form.

8. The method of claim 1 further comprising the step of at least one professional affiliated with the system administrator determines when case is ready for submission to selected panel of participating medical professionals.

9. The method of claim 1 further comprising the step of providing the user submitted information to the panel of selected medical professionals.

10. The method of claim 1 further comprising the step of providing the user submitted information to the panel of selected medical professionals via the internet.

11. The method of claim 1 further comprising the step of selecting a panel of medical professionals for participation in the medical consultation from the database based on the qualifications of the medical professionals in the database.

12. The method of claim 1 wherein the database includes information about the potential participating medical professionals in addition to the qualifications of the medical professionals, further comprising the step of selecting a panel of medical professionals for participation in the medical consultation based upon information in the database about the medical professionals in addition to the qualifications of the medical professionals.

13. The method of claim 1 further comprising the step of system uses software to select panel of medical professionals for participation in the medical consultation based upon the nature of the consultation and stored information in the database.

14. The method of claim 1 further comprising the step of parsing the user submitted information against defined criteria using a software program to determine if user submitted information meets the minimum defined criteria.

15. The method of claim 1 further comprising the step of displaying consensus information in real time as responses from medical professionals in the selected panel are received by the system.

16. The method of claim 1 further comprising the step of creating a graphical display of the consensus of the responses of the medical professionals and displaying same in real time.

17. The method of claim 1 wherein medical professionals in the selected panel respond using surveys submitted to the system via the internet.

18. The method of claim 1 further comprising the step of professionals affiliated with the system periodically check for new user submissions.

19. The method of claim 1 further comprising the step of utilizing the responses from the medical professionals in the selected panel to determine an acceptable standard of health care.

20. The method of claim 1 further comprising the step of utilizing the responses from the medical professionals in the selected panel to determine an acceptable standard of health care to determine the strength of a medical malpractice claim.

21. The method of claim 1 further comprising the step of utilizing the responses from the medical professionals in the selected panel to determine an assessment of newsworthy medical information.

22. The method of claim 1 further comprising the step of utilizing the responses from the medical professionals in the selected panel to determine an assessment of government health policies.

23. The method of claim 1 further comprising the step of utilizing the responses from the medical professionals in the selected panel to determine a consensus as to the acceptability of a new drug or medical device.

24. The method of claim 1 further comprising the step of utilizing the responses from the medical professionals in the selected panel to determine an assessment of competitive drugs.

25. The method of claim 1 further comprising the step of utilizing the responses from the medical professionals in the selected panel to determine an assessment of public health officials.

26. The method of claim 1 further comprising the step of utilizing the responses from the medical professionals in the selected panel to determine an assessment of personal physician practices.

27. The method of claim 1 further comprising the step of selecting the panel of medical professionals from a group of physicians, nurses, chiropractors and/or pharmacists.

28. An online method of providing online medical consultation services utilizing a computer-implemented system connected to the internet to obtain quantitative and qualitative medical opinions from a panel of selected medical professionals, the method comprising the steps of:
  (a) creating a database of potential participating medical professionals, along with information about each potential participating medical professional, including the qualifications of the potential participating medical professional;
  (b) user seeking a medical consultation accesses the system;
  (c) user submits information regarding the desired medical consultation;
  (d) system selects a panel of medical professionals qualified to provide desired medical consultation based upon information in the database;
  (e) question(s) based on user submitted information and user submitted information are provided to the medical professionals in the selected panel;
  (f) medical professionals in the selected panel formulate response(s) to provided question(s) and comments regarding user submitted information;
  (g) responses and comments from the medical professionals in the selected panel are forwarded to the system; and
  (h) system calculates the degree of consensus of responses to questions, and displays same, along comments from the medical professionals, on a system website accessible to the user.

29. The method of claim 28 wherein user seeking a medical consultation accesses the system via the internet.

30. The method of claim 28 wherein user seeking a medical consultation submits information regarding the desired medical consultation to system via the internet.

31. The method of claim 28 wherein a case submission form is provided to user seeking a medical consultation and user submits information regarding the desired medical consultation to system using the case submission form.

32. The method of claim 31 wherein user submits information regarding the desired medical consultation to system over the internet using the case submission form.

33. The method of claim 28 further comprising the step of determining when case is ready for submission to selected panel of medical professionals.

34. The method of claim 28 further comprising the step of selecting a panel of medical professionals for participation in the medical consultation from the database based on the qualifications of the medical professionals.

35. The method of claim 28 wherein the database including information about the potential participating medical professionals in addition to the qualifications of the medical professionals, further comprising the step of selecting a panel of medical professionals for participation in the medical consultation based upon information in the database about the medical professionals in addition to the qualifications of the medical professionals.

36. The method of claim 28 further comprising the step of system uses software to select panel of medical professionals for participation in the medical consultation based upon the nature of the medical consultation and information about the medical professionals in the database.

37. The method of claim 28 further comprising the steps of creating defined criteria and parsing the user submitted information against the defined criteria using a software program to determine if user submitted information meets minimum defined criteria.

38. The method of claim 28 further comprising the step of displaying consensus information in real time as responses from medical professionals in the selected panel are received by the system.

39. The method of claim 28 wherein medical professionals in the selected panel respond to the system using surveys submitted to the system via the internet.

40. The method of claim 28 further comprising the step of creating a graphical display of the consensus of the responses from the medical professionals in the selected panel and displaying same in real time.

41. The method of claim 28 further comprising the step of at least one professional affiliated with the system periodically checks for new user submissions.

42. The method of claim 28 further comprising the step of utilizing the responses from the medical professionals in the selected panel to determine an acceptable standard of health care.

43. The method of claim 28 further comprising the step of utilizing the responses from the medical professionals in the selected panel to determine an acceptable standard of health care to determine the strength of a medical malpractice claim.

44. The method of claim 28 further comprising the step of utilizing the responses from the medical professionals in the selected panel to determine an assessment of newsworthy medical information.

45. The method of claim 28 further comprising the step of utilizing the responses from the medical professionals in the selected panel to determine an assessment of government health policies.

46. The method of claim 28 further comprising the step of utilizing the responses from the medical professionals in the selected panel to determine a consensus as to the acceptability of a new drug or medical device.

47. The method of claim 28 further comprising the step of utilizing the responses from the medical professionals in the selected panel to determine an assessment of competitive drugs.

48. The method of claim 28 further comprising the step of utilizing the responses from the medical professionals in the selected panel to determine an assessment of public health officials.

49. The method of claim 28 further comprising the step of utilizing the responses from the medical professionals in the selected panel to determine an assessment of personal physician practices.

50. The method of claim 28 further comprising the step of selecting the panel of medical professionals from a group of physicians, nurses, chiropractors and/or pharmacists.

51. A computer-implemented system for providing medical consultation services connected to the internet, integrated with human resources provided by professionals affiliated with the system, to form a consensus of opinions by a panel of medical professionals selected by the system but not provided with financial incentives which could bias their decision making, the system comprising:
  (a) means for creating a database of potential participating medical professionals, along with information about each the potential participating medical professionals, including the qualifications of the potential participating medical professionals;
  (b) means for user seeking medical consultation services to accesses the system;
  (c) means for user to electronically submit information to the system regarding the desired medical consultation services such that at least one professional affiliated with the system can review the information submitted by the user and structure one or more questions, based upon the user submitted information, for consideration by a panel of selected medical professionals;
  (d) means for selecting a panel of medical professionals qualified to provide response(s) to the structured question(s) based upon information in the database;
  (e) means for providing the structured question(s) to the medical professionals in the selected panel such that medical professionals in the selected panel can review the structured question(s) and create responses thereto;
  (f) means for electronically forwarding the responses from the medical professionals in the selected panel to the system;
  (g) means for compiling the responses forwarded to the system by the medical professionals in the selected panel;
  (h) means for calculating the degree of consensus of the responses; and
  (i) means for displaying the calculated consensus on a system website accessible to the user.

52. The system of claim 51 further comprising means for professional(s) affiliated with the system to gather additional information in order to structure question(s).

53. The system of claim 51 further comprising means for professional(s) affiliated with the system to interact with user to gather additional information about the desired medical consultation.

54. The system of claim 51 wherein said means for user seeking medical consultation services to accesses the system comprises the internet.

55. The system of claim 51 wherein said means for user seeking medical consultation services to submit information regarding the desired medical consultation to the system comprises the internet.

56. The system of claim 51 further comprising a case submission form and means for providing said case submission form to user seeking medical consultation services.

57. The system of claim 56 further comprising means for user to submit said case submission form to the system.

58. The system of claim 57 wherein means for user to submit said case submission form to the system comprises the internet.

59. The system of claim 51 wherein profession(s) affiliated with the system determine when case is ready for submission to selected panel of medical professionals.

60. The system of claim 51 further comprising means for submitting the user submitted information to the panel of selected medical professionals.

61. The system of claim 60 wherein said means for providing the user submitted information to the panel of selected medical professionals comprises the internet.

62. The system of claim 51 further comprising means for selecting a panel of medical professionals for participation in the medical consultation from the database based on the qualifications of the medical professionals in the database.

63. The system of claim 51 wherein said database including information about potential participating medical professions in addition to the qualifications of the medical professionals, further comprising means for selecting a panel of medical professionals for participation in the medical consultation based upon information in the database about the medical professionals in addition to the qualifications of the medical professionals.

64. The system of claim 51 further comprising software for selecting a panel of medical professionals for participation in the medical consultation based upon the nature of the medical consultation and stored information in the database.

65. The system of claim 51 further comprising means for creating minimum defined criteria and software for parsing the user submitted information against said minimum defined criteria to determine if user submitted information meets said minimum defined criteria.

66. The system of claim 51 further comprising means for displaying consensus information in real time as responses from medical professionals in the selected panel are received by the system.

67. The system of claim 51 further comprising means for creating a graphical display of the consensus of the responses of the medical professionals and for displaying same in real time.

68. The system of claim 51 wherein said means for medical professionals in the selected panel to forward responses comprises surveys submitted to the system via the internet.

69. The system of claim 51 wherein professional(s) affiliated with the system periodically check for new user submissions.

70. The system of claim 51 wherein the panel of medical professionals is selected from a group of physicians, nurses, chiropractors and/or pharmacists.

71. An online system for providing online medical consultation services including quantitative and qualitative medical opinions from a panel of selected medical professionals, the system comprising:
(a) creating a database of potential participating medical professionals, along with information about each the potential participating medical professionals, including the qualifications of the potential participating medical professionals;
(b) means for a user seeking medical consultation services to access the system;
(c) means for user to electronically submit information to the system regarding the desired medical consultation services;
(d) means for selecting a panel of medical professionals qualified to provide the desired medical consultation services based upon information in the database;
(e) means for electronically providing question(s) based on the user submitted information, and the user submitted information, to the medical professionals in the selected panel such that the medical professionals in the selected panel formulate response(s) to provided question(s) and comments regarding user submitted information;
(f) means for electronically forwarding the responses and comments from the medical professionals in the selected panel to the system;
(g) means for calculating the degree of consensus of forwarded responses to questions;
(h) means for displaying said calculated consensus on a system website accessible to user; and
(i) means for displaying said comments forwarded from the medical professionals on a system website accessible to the user.

72. The system of claim 71 wherein said means for user seeking medical consultation services to accesses the system comprises the internet.

73. The system of claim 71 wherein said means for user seeking medical consultation services to submit information regarding the desired medical consultation services to system comprises the internet.

74. The system of claim 71 further comprising a case submission form and means for providing said case submission form to the user seeking medical consultation services.

75. The system of claim 74 further comprising means for the user to submit said case submission form to the system.

76. The system of claim 75 wherein said means for submitting said case submission form to the system comprises the internet.

77. The system of claim 71 further comprising means for determining when case is ready for submission to selected panel of medical professionals.

78. The system of claim 71 further comprising means for selecting a panel of medical professionals for participation in the medical consultation from said database based on the qualifications of the medical professionals.

79. The system of claim 71 wherein said database includes information about the potential participating medical professionals in addition to the qualifications of the medical professionals, further comprising means for selecting a panel of medical professionals for participation in the medical consultation based upon information in said database about the medical professionals in addition to the qualifications of the medical professionals.

80. The system of claim 71 further comprising software for selecting a panel of medical professionals for participation in the medical consultation based upon the nature of the medical consultation and information about the medical professionals in said database.

81. The system of claim 71 further comprising means for creating minimum defined criteria and means for parsing the user submitted information against the said minimum defined criteria to determine if user submitted information meets minimum defined criteria.

82. The system of claim 71 wherein said means for calculating the degree of consensus calculates the degree of consensus in real time, as responses from medical professionals in the selected panel are received by the system.

83. The system of claim 71 further comprising a survey and wherein medical professionals in the selected panel respond to the system using said survey.

84. The system of claim 83 wherein said survey is submitted to the system via the internet.

85. The system of claim 71 further comprising means for creating a graphical display of said calculated consensus of the responses from the medical professionals in the selected panel.

86. The system of claim 85 further comprising means for displaying said graphical display in real time.

87. The system of claim 71 further wherein the system is periodically checked for new user submissions.

88. The system of claim 71 further comprising means for selecting the panel of medical professionals from a group of physicians, nurses, chiropractors and/or pharmacists.

* * * * *